(12) United States Patent
An et al.

(10) Patent No.: US 8,575,331 B2
(45) Date of Patent: *Nov. 5, 2013

(54) SYNTHESIS AND USE OF 2'-SUBSTITUTED-N6-MODIFIED NUCLEOSIDES

(75) Inventors: Haoyun An, Carlsbad, CA (US); Kanda Ramasamy, Aliso Viejo, CA (US); Stephanie Shaw, Rowland Heights, CA (US)

(73) Assignee: Valeant Pharmaceuticals North America, Bridgewater, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/876,997

(22) Filed: Sep. 7, 2010

(65) Prior Publication Data
US 2011/0196144 A1    Aug. 11, 2011

Related U.S. Application Data

(63) Continuation of application No. 10/542,235, filed as application No. PCT/US2004/001125 on Jan. 15, 2004, now Pat. No. 7,799,908.

(60) Provisional application No. 60/440,666, filed on Jan. 15, 2003.

(51) Int. Cl.
  *C07H 19/167*    (2006.01)
  *C07H 19/173*    (2006.01)

(52) U.S. Cl.
  USPC .................................................. 536/27.6

(58) Field of Classification Search
  None
  See application file for complete search history.

(56) References Cited

U.S. PATENT DOCUMENTS

| 7,799,908 B2 * | 9/2010 | An et al. ............... 536/27.6 |
| 2004/0063658 A1 * | 4/2004 | Roberts et al. ............ 514/45 |

FOREIGN PATENT DOCUMENTS

| WO | WO03/062256 | * | 7/2003 |
| WO | WO03062256 | | 7/2003 |
| WO | WO2004/028481 | * | 4/2004 |
| WO | WO2004028481 A2 | | 4/2004 |

OTHER PUBLICATIONS

Brodfuehrer et al., "A highly stereoselective route to calcitriol lactone" J, Org. Chem. 50:2598-2600 (1 985).
Cook and Greenberg, "A general synthesis of C2'-deuteriated ribonucleosides" J, Org. Chem. 5914704-4706 (1 994).
Franchetti et al., "2'-C-methyl analogues of selective adenosine receptor agonists: Synthesis and binding studies" J, Med, Chem. 41 : 1708-1715 (1 998).
Harry-O'kuru et al., "A short, flexible route toward 2'-C-branched ribonucleosides" J, Org. Chem. 6211 754-1 759 (1 997).
Lohmann et al., "Replication of a subgenomic hepatitis C virus RNAs in a hepatoma cell line" Science 285:IIO-113 (1 999).
Wolfe and Harry-O'kuru "A concise synthesis of 2'c-methylribonucleosides" Tetrahedron Lett. 421761 1-761 4 (1 995).

* cited by examiner

*Primary Examiner* — Traviss C McIntosh, III
(74) *Attorney, Agent, or Firm* — Len S. Smith; Judith U. Kim; Matthew S. Bodenstein

(57) ABSTRACT

An improved method of preparing a sugar modified nucleoside analog includes a protocol in which a hydroxy group of a sugar is selectively deprotected and oxidized prior to nucleophilic modification of the corresponding carbonyl group. The modified sugar is then coupled to a heterocyclic base that is modified with a dual nucleophilic reagent in a further step that provides N6-modified adenosine analogs with high stereoselectivity.

14 Claims, 2 Drawing Sheets

Scheme 1

Scheme 2

SYNTHESIS AND USE OF 2'-SUBSTITUTED-N6-MODIFIED NUCLEOSIDES

This application is a continuation of U.S. application Ser. No. 10/542,235, filed Jul. 15, 2005, which is a national stage filing under 35 U.S.S.§371 of International Patent Application Serial No. PCT/US2004/001125, which was filed on Jan. 15, 2004, and which was published in English under PCT Article 21(2) as WO 2004/065398 on Aug. 5, 2004, which International Patent Application claims benefit of priority of U.S. Provisional Application Ser. No. 60/440,666, filed Jan. 15, 2003, the contents of each of which is incorporated herein by reference in its entirety.

FIELD OF THE INVENTION

The field of the invention is synthesis of nucleosides, their analogs, and uses thereof.

BACKGROUND OF THE INVENTION

There are numerous methods known in the art to prepare nucleoside analogs, wherein such compounds may include modifications on the heterocyclic base as well as on the sugar moiety. In some approaches, modifications are introduced into the already synthesized nucleoside to yield the desired nucleoside analog, while in other approaches the sugar portion is modified and then coupled to the heterocyclic base (which may or may not be modified) to generate the desired nucleoside analog.

However, and particularly where the desired nucleoside analogs include reactive groups (e.g., OH groups in the sugar, $NH_2$ group in the heterocyclic base), various difficulties are frequently encountered. For example, where the modification of the heterocyclic base and/or the sugar portion in a nucleoside requires relatively strong acidification or other relatively harsh conditions, the glycosidic bond in the nucleoside may be destroyed in the process. In another example, modification reagents may react not only with the desired functional group(s) in the heterocyclic base, sugar, and/or nucleoside, but may also modify reactive groups where those are unprotected. Moreover, even where relatively high selectivity may be achieved using protecting groups and modification reagents using particular reaction conditions, such conditions may lead to subsequent problems in isolation, isomeric purification, and/or instability of the desired product.

Thus, although there are numerous methods known in the art to produce nucleoside analogs, all or almost all of them suffer from one or more disadvantages. Therefore, there is still a need for improved methods and compositions for synthesized nucleoside analogs, and especially those with a 2'-beta-methyl modified sugar and an $N^6$-modified adenine base.

SUMMARY OF THE INVENTION

The present invention is generally directed to N6-substituted adenosine nucleoside analogs, and their preparation and use. Especially preferred nucleoside analogs are prepared from a precursor with an electrophilic center that is reacted with a dual nucleophilic reagent under conditions such that the reaction product is formed with high selectivity in which only one of the two nucleophilic groups of the dual nucleophilic reagent reacts with the heterocyclic base.

In one preferred aspect of the inventive subject matter, a method of synthesizing an N6-substituted adenosine analog includes one step in which is provided a dual nucleophilic reagent having a first nucleophilic group and a second nucleophilic group, and an adenosine analog having a leaving group in the 6-position. In another step, the dual nucleophilic reagent is reacted with the adenosine under a reaction condition such that the leaving group is replaced by the first nucleophilic group with a selectivity of at least 90%, wherein the reaction condition includes reacting the dual nucleophilic reagent and the heterocyclic base in a non-basic environment under a protective atmosphere and a temperature of at least 40° C.

Further preferred dual nucleophilic reagents will have a structure of $R_1R_2N-NR_3R_4$, or $H_2N-OR_1$, wherein $R_1$, $R_2$, $R_3$, and $R_4$ are independently selected from the group consisting of H, alkyl, substituted alkyl, alkenyl, substituted alkenyl, alkynyl, substituted alkynyl, aryl, substituted aryl, heterocycle, substituted heterocycle, acyl, and substituted acyl. Suitable reaction conditions for hydrazine-type reagents will therefore include those in which the non-basic environment comprises at least one of ethanol and methylene chloride, and wherein the temperature is at least 70° C. Similarly, suitable reaction conditions for hydroxyamine-type reagents will therefore include those in which the non-basic environment comprises at least one of water and ethanol, and wherein the temperature is at least 70° C.

It is especially preferred that the step of reacting the dual nucleophilic reagent with the adenosine is performed in a single step and provides a yield of at least 90% of the N6-substituted adenosine analog, and it is still further preferred that the adenosine analog is 6-Chloro-9H-(2'-β-C-methyl-β-D-ribofuranosyl)purine, wherein the 2'-β-C-methyl group of the 6-Chloro-9H-(2'-β-C-methyl-β-D-ribofuranosyl)purine is preferably introduced by a step of reacting a protected D-2-ketoribofuranose with methyl magnesium bromide.

In a further aspect of the inventive subject matter, contemplated compounds obtained by synthetic routes presented herein will include those having a structure according to Formula I:

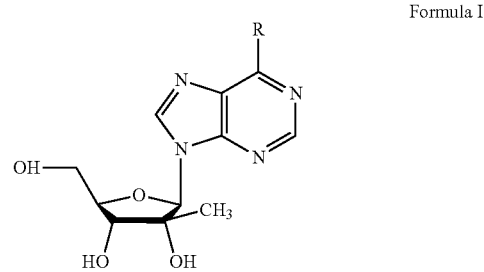

Formula I wherein R is selected from the group consisting of $NHNH_2$, $N(CH_3)NH_2$, $N(CH_3)OH$, $N(CH_2CH_3)NH_2$, $NHOH$, $NHOCH_3$, $NHOCH_2CH_3$, $NHN(CH_3)_2$, $N(CH_3)NHCH_3$, $NHNHCH_3$, $NHNHOCH_3$, and $NHNHCOOCH_3$.

Various objects, features, aspects and advantages of the present invention will become more apparent from the detailed description of preferred embodiments of the invention given below.

DETAILED DESCRIPTION

The inventors discovered a synthetic procedure in which 2'-substituted $N^6$-modified nucleosides and their analogs can be prepared in high yields and purity under conditions that favor highly selective reaction of a precursor with only one or tow reactive centers in a dual nucleophilic reagent. Furthermore, contemplated procedures will advantageously reduce undesired oxidation of various desired reaction products.

With respect to the sugar portion of contemplated molecules, it should be appreciated that the procedures according to the inventive subject matter will be synthesized in a large and practical scale using selective deprotection and oxidation via a Dess-Martin reagent. Such reaction conditions are thought to allow fast and efficient oxidation without generation of undesired side products that would otherwise require one or more purification/isolation steps.

Furthermore, and with respect to the selective modification of the N6-position in a heterocyclic base (and most preferably of adenine), it should be recognized that contemplated processes will provide conditions under which a dual nucleophilic reagent will react with high selectivity to provide the desired product. Thus, as one exemplary desired product, it should be appreciated that 2'-beta-methyl-$N^6$-amino-$N^6$-methylribofuranosyladenosine may be selectively prepared in several steps from a sugar component and a heterocyclic base.

Figure 1:
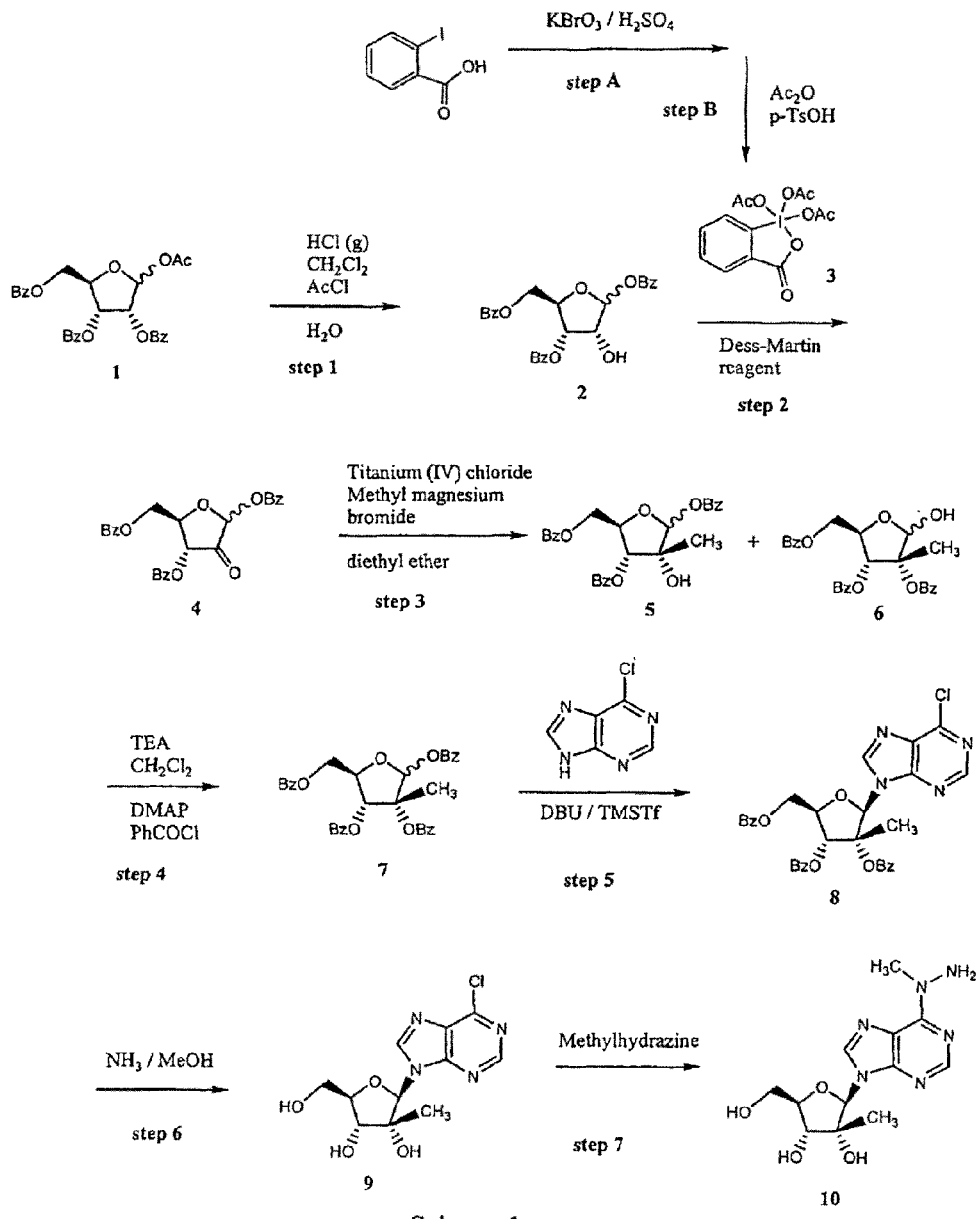
FIG. 1 is a schematic of one exemplary synthetic route according to the inventive subject matter in which (a) a 2'-modified sugar is prepared using selective deprotection and oxidation of a hydroxy group, (b) the so obtained protected keto-sugar is regioselectively converted to the corresponding beta-substituted sugar, (c) the sugar is coupled to a modified heterocyclic base to form the corresponding modified nucleoside, and (d) the modified nucleoside is reacted with a dual nucleophilic reagent under conditions to provide selective reaction for generation of the desired reaction product.

In one exemplary synthetic route, as shown in FIG. 1, the inventors discovered that suitably protected sugars (e.g., via benzoyl groups), and particularly furanose sugars can be deprotected at the 2'-position with relatively high selectivity under mild conditions to generate the corresponding 2'-deprotected sugar. In a further step, the so generated 2'-deprotected sugar is then reacted with a Dess-Martin reagent to selectively oxidize the 2'-hydroxy group to a 2'-keto group while maintaining protection of the remaining hydroxy groups in the sugar. Reaction of the so generated carbonyl carbon with a nucleophile, and most preferably with organometallic reagents, including Titanium or Grignard reagents (e.g., substituted or unsubstituted alkylMgBr), will afford the 2'-beta-modified sugar with high stereoselectivity (under concomitant deprotection of the 1'-hydroxy group in at least part of the products). Thus, it should be recognized that the introduction of the 2'-β-C-methyl group is performed without purification of the reaction mixture producing the D-2-ketoribofuranose (see also experimental section). After protecting the unprotected hydroxyl group in either the 1'- or 2'-alpha-position using standard procedures, the 2'-beta-modified sugar is coupled to a heterocyclic base using DBU and TMSOTf as coupling reagents in large Scale to yield the corresponding 2'-modified beta-nucleoside analog in high yield although the 2'-beta-methyl group generally effects the stereoselectivity for the glycosylation.

Remarkably, selective oxidation and alkylation in beta-position using the procedures according to the inventive subject matter results in a substantially stereochemically pure (i.e., at least 90%, more typically at least 95%, and most typically at least 98%) 2'-beta alkylated product. Where needed, the so obtained product is then typically re-protected and coupled to a heterocyclic base using standard protocols (see e.g., Protective Groups in Organic Synthesis by Peter G. M. Wuts, Theodora W. Greene, John Wiley & Sons; ISBN: 0471160199).

In another preferred aspect of synthesis of contemplated compounds, it is generally preferred that the so produced 2'-beta modified nucleoside analog includes one or more leaving groups at the heterocyclic base that can be modified in a reaction that will retain the remaining reactive groups (protected and/or unprotected) and that will retain the glycosidic bond. An exemplary leaving group, as depicted in FIG. 1, is chlorine, which is replaced by a nucleophile in a nucleophilic substitution.

As used herein, the terms "heterocycle" and "heterocyclic base" are used interchangeably herein and refer to any compound in which a plurality of atoms form a ring via a plurality of covalent bonds, wherein the ring includes at least one atom other than a carbon atom. Particularly contemplated heterocyclic bases include 5- and 6-membered rings with nitrogen, sulfur, or oxygen as the non-carbon atom (e.g., imidazole, pyrrole, triazole, dihydropyrimidine). Further contemplated heterocycles may be fused (i.e., covalently bound) to another ring or heterocycle, and are thus termed "fused heterocycle" as used herein. Especially contemplated fused heterocycles include a 5-membered ring fused to a 6-membered ring (e.g., purine, pyrrolo[2,3-d]pyrimidine), and a 6-membered ring fused to another 6-membered or higher ring (e.g., pyrido[4, 5-d]pyrimidine, benzodiazepine).

Still further contemplated heterocyclic bases may be aromatic, or may include one or more double or triple bonds. Moreover, contemplated heterocyclic bases may further include one or more substituents other than hydrogen, and especially contemplated substituents include those referenced below. Contemplated heterocycles or substituted heterocycles are typically attached directly to nucleoside bases or sugars, but coupling of the heterocyclic base to the sugar may also include a linker moiety with at least 1-4 atoms between the heterocyclic base and the sugar.

As further used herein, the term "sugar" refers to all carbohydrates and derivatives thereof, wherein particularly contemplated derivatives include deletion, substitution or addition of a chemical group in the sugar. For example, especially contemplated deletions include 3'-deoxy sugars. Especially contemplated substitutions include replacement of the ring-oxygen with sulfur, methylene, or nitrogen, or replacement of a hydroxyl group with a halogen, an amino-, sulfhydryl-, or methyl group, and especially contemplated additions include methylene phosphonate groups. Further contemplated sugars also include sugar analogs (i.e., not naturally occurring sugars), and particularly carbocyclic ring systems. The term "carbocyclic ring system" as used herein refers to any molecule in which a plurality of carbon atoms form a ring, and in especially contemplated carbocyclic ring systems the ring is formed from 3, 4, 5, or 6 carbon atoms. Examples of these and further preferred sugars are given below.

The terms "alkyl" and "unsubstituted alkyl" are used interchangeably herein and refer to any linear, branched, or cyclic hydrocarbon in which all carbon-carbon bonds are single bonds'. The term "substituted alkyl" as used herein refers to any alkyl that further comprises a functional group, and particularly contemplated functional groups include nucleophilic (e.g., —$NH_2$, —OH, —SH, —NC, etc.) and electrophilic groups (e.g., C(O)OR, C(X)OH, etc.), polar groups (e.g., —OH), non-polar groups (e.g., aryl, alkyl, alkenyl, alkynyl, etc.), ionic groups (e.g., —$NH_3^+$), and halogens (e.g., —F, —Cl), and all chemically reasonable combinations thereof. The terms "alkenyl" and "unsubstituted alkenyl" are used interchangeably herein and refer to any linear, branched, or cyclic alkyl with at least one carbon-carbon double bond. The term "substituted alkenyl" as used herein refers to any alkenyl that further comprises a functional group, and particularly contemplated functional groups include those discussed above.

Furthermore, the terms "alkynyl" and "unsubstituted alkynyl" are used interchangeably herein and refer to any linear, branched, or cyclic alkyl or alkenyl with at least one carbon-carbon triple bond. The term "substituted alkynyl" as used herein refers to any alkynyl that further comprises a functional group, and particularly contemplated functional groups include those discussed above. The terms "aryl" and "unsubstituted aryl" are used interchangeably herein and refer to any aromatic cyclic, alkenyl, or alkynyl. The term "substituted aryl" as used herein refers to any aryl that further comprises a functional group, and particularly contemplated functional groups include those discussed above. The term "alkaryl" is employed where the aryl is further covalently bound to an alkyl, alkenyl, alkynyl, or alkynyl.

Thus, the term "substituted" as used herein also refers to a replacement of a chemical group or substituent (typically H or OH) with a functional group, and particularly contemplated functional groups include nucleophilic (e.g., —$NH_2$, —OH, —SH, —NC, etc.) and electrophilic groups (e.g., C(O)OR, C(X)OH, etc.), polar groups (e.g., —OH), non-polar groups (e.g., aryl, alkyl, alkenyl, alkynyl, etc.), ionic groups (e.g., —$NH_3^+$), and halogens (e.g., —F, —Cl), and all chemically reasonable combinations thereof.

It should generally be recognized that all nucleophilic reagents are considered suitable for use herein. However, particularly preferred nucleophilic reagents include compounds in which two or more nucleophilic centers are present (i.e., dual nucleophilic reagents). Among other reagents, especially suitable dual nucleophilic reagents include those in which the first nucleophilic group is a primary or secondary amine group, and in which the second nucleophilic group is a hydroxyl group, ether group, or a primary or secondary amine.

Therefore, particularly preferred nucleophilic reagents include various substituted and unsubstituted hydrazines and hydroxyamines with the general formula $R_1R_2N$—$NR_3R_4$ and $R_1R_2N$—$OR_5$, in which $R_1$, $R_2$, $R_3$, $R_4$, and $R_5$ are independently selected from the group consisting of H, allyl, substituted alkyl, alkenyl, substituted alkenyl, alkynyl, substituted alkynyl, aryl, substituted aryl, heterocycle, substituted heterocycle, acyl, and substituted acyl. Exemplary dual nucleophilic reagents therefore include $NH_2NH_2$, $NH_2N(CH_3)_2$, $NHCH_3NHCH_3$, $NH_2NHCH_3$, $NH_2NHC(O)CH_3$, $NH_2NHC(O)OCH_3$, $NH_2OCH_2CH_3$, $NH_2NHR$, $NH(Boc)NHR$, NHRNHR, $NH_2OH$, NHROH, NHROR, $NH_2OR$, and $NR_2OH$, where R is independently H, C1-C5 alkyl/alkenyl, alkenyl, or C5-C15 aryl.

It should be particularly noted that contemplated synthetic protocols will provide substantially stereoselective pure (i.e., at least 90%, more typically at least 95%, and most typically at least 98%) reaction products. For example, where the dual nucleophilic reagent is a monosubstituted hydrazine of the general formula $R_1HN$—$NH_2$ (with $R_1$ as defined above), the nitrogen of the substituted amino group will act as the nucleophilic group under conditions according to the inventive subject matter. Indeed, a person of ordinary skill in the art would rather expect that the nitrogen atom of the NH2 group would act (at least to some extent) as a nucleophilic center due to reduced steric hindrance. However, under the reaction conditions contemplated herein, this is clearly not the case. Similarly, where the dual nucleophilic reagent is a monosubstituted hydroxyamine of the general formula $R_1O$—$NH_2$, HO—$NR_1H$, or $R_1O$—$NR_2H$ (with $R_1$ and $R_2$ as defined above), the nitrogen of the amino group will act as the nucleophilic group under conditions according to the inventive subject matter, while the oxygen will typically not react to a significant degree (i.e., less than 5%, more typically less than 3%, and most typically less than 2%).

The inventors discovered that in reaction protocols according to the inventive subject matter the OH group is more nucleophilic than an $NH_2$ group under strong basic conditions, but that the $NH_2$ group is more nucleophilic than OH under weak basic conditions, and the inventors eventually discovered that the nitrogen (substituted where substituted hydrazine is used, or nitrogen in hydroxyamines) reacted first and exclusively with the nucleoside electrophile without adding any base. Remarkably, the inventors further observed that under such reaction conditions the reaction conditions for the dual nucleophilic reagent also provide a deprotection of the protecting groups at the sugar (which can take place in the same reaction mixture in the same vessel).

Figure 2:
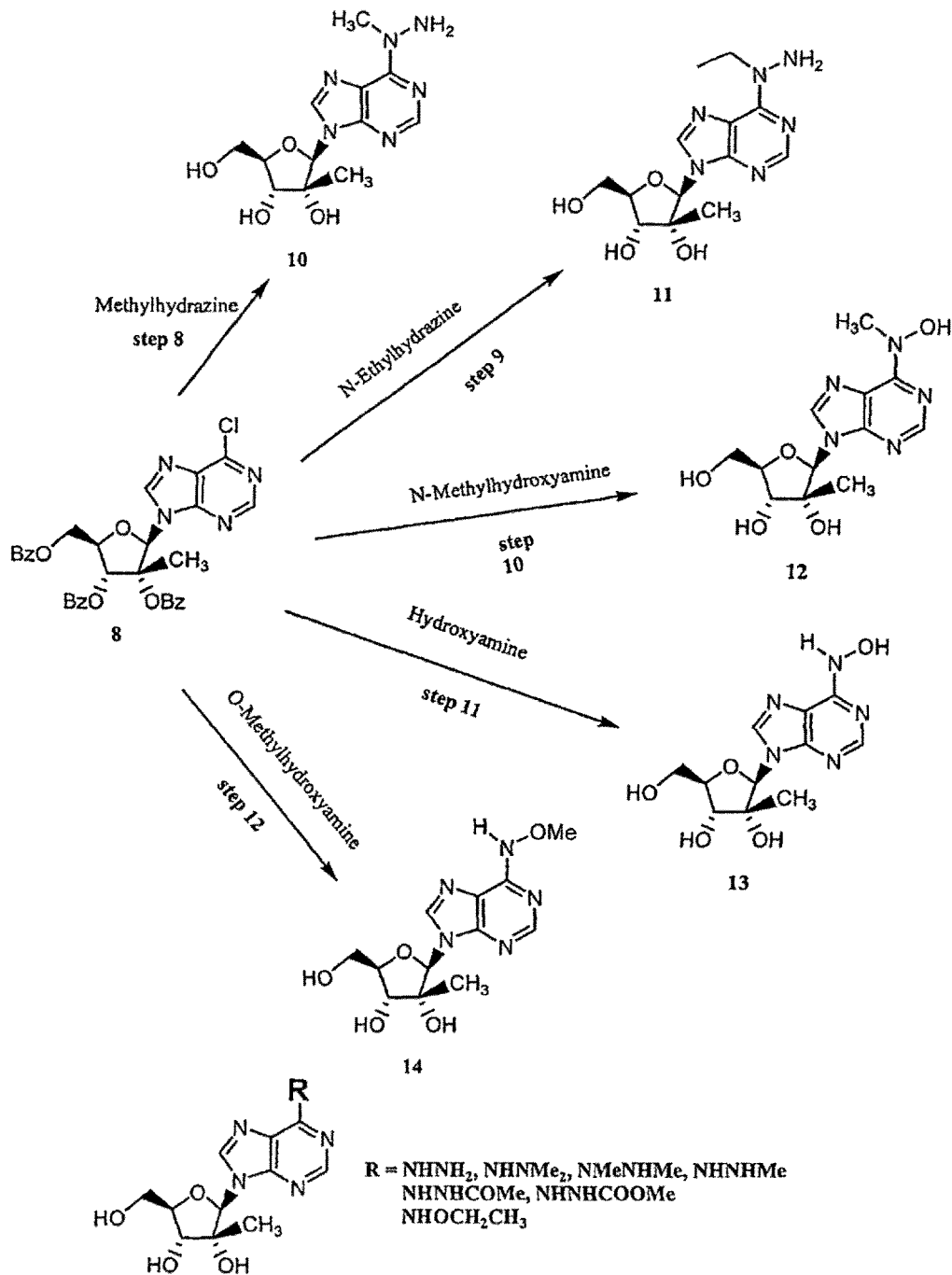
FIG. 2 is a schematic of another exemplary synthetic route according to the inventive subject matter in which a protected nucleoside is modified in the 6-position at the heterocyclic base while deprotecting the protected nucleoside with the modification reagent.

Thus, in one approach, it is contemplated that the nucleoside analog, after coupling the sugar to the heterocyclic base, is first deprotected and that the deprotected nucleoside analog is then reacted with the nucleophilic reagent to yield the desired deprotected 2'-methyl-6-substituted adenosine. Alternatively, in another approach the inventors discovered that the nucleophilic reagent may also be employed to remove one or more of the protecting groups at the same time in the step of replacing the leaving group as depicted in FIG. 2. Viewed from another perspective, the inventors discovered that the 6-position modifying agent (i.e., the nucleophilic agent) may also act as a deprotectant. This second strategy saves one step, and gives a high quality, high yield product that is easily purified. Therefore, this later strategy is superior to the first strategy, although both approaches are effectively utilized for the synthesis of this type of derivatives.

It should therefore be especially appreciated that contemplated synthetic routes provide selective and mild reactive conditions to form the 2'-modified sugar, while at the same time significantly reducing oxidative damage to the compounds by employing the 6-position modifying agent as a deprotectant when compared to other methods.

Consequently, the inventors contemplate a method of synthesizing an N6-substituted adenosine analog in which in one step a dual nucleophilic reagent is provided having a first nucleophilic group and a second nucleophilic up, and an adenosine analog having a leaving group in 6-position. In another step, the dual nucleophilic reagent is reacted with the adenosine under a reaction condition such that the leaving group is replaced by the first nucleophilic group with a selectivity of at least 90% (more preferably at least 95%, even more preferably at least 97%) and wherein the reaction condition comprises a reaction of the dual nucleophilic reagent with the adenosine in a non-basic environment under a protective atmosphere and a temperature of at least 40° C.

The term "adenosine analog" as used herein generally refers to a nucleoside in which the nucleoside has a sugar that is coupled to a heterocyclic base. Preferred heterocyclic bases in contemplated adenosine analogs will have a purine scaffold, in which one or more nitrogen atoms are optionally replaced by a (substituted) carbon atom, and in which the sugar is substituted at the 2'-position (preferably in beta orientation). Thus, in further preferred aspects of the inventive subject matter, a N6-substituted adenosine analog is a purine nucleoside in which the purine moiety has a substituted amino group in 6-position of the purine scaffold.

As also used herein, the term "non-basic environment" refers to an environment for reacting the heterocyclic base with a first nucleophilic group of the dual nucleophilic reagent under conditions that either entirely exclude addition of a base, or maintain addition of a base to the reaction medium below a level that would enable the undesirable reaction of the second nucleophilic group to form at least 10% (and more typically at least 5%) product in which the second group has reacted with the heterocyclic base.

As still further used herein, the term "protective atmosphere" refers to any atmosphere that replaces ambient air in the reaction vessel with a gas substantially depleted (i.e., less than 1 vol %, more typically less than 0.1 vol %) of oxygen. Thus, suitable protective atmospheres include pure argon, nitrogen, or helium.

Where the dual nucleophilic reagent has a structure of $R_1R_2N-NR_3R_4$, with $R_1$, $R_2$, $R_3$, and $R_4$ independently selected from the group consisting of H, alkyl, substituted alkyl, alkenyl, substituted alkenyl, alkynyl, substituted alkynyl, aryl, substituted aryl, heterocycle, substituted heterocycle, acyl, and substituted acyl, it is especially preferred that the non-basic environment comprises at least one of ethanol and methylene chloride, and that the temperature is at least 70° C.

On the other band, where the dual nucleophilic reagent has a structure of $H_2N-OR_1$, and wherein $R_1$ is selected from the group consisting of H, alkyl, substituted alkyl, alkenyl, substituted alkenyl, alkynyl, substituted alkynyl, aryl, substituted aryl, heterocycle, substituted heterocycle, acyl, and substituted acyl, it is preferred that the non-basic environment comprises at least one of water and ethanol, and wherein the temperature is at least 70° C.

Contemplated Compounds

It is generally contemplated that compounds obtained by procedures according to the inventive subject matter will include those having a structure as depicted in Formula I below:

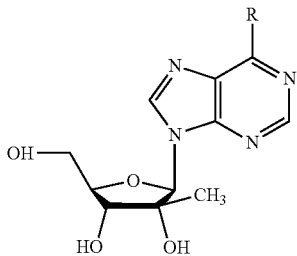

Formula I wherein R is selected from the group consisting of $NHNH_2$, $N(CH_3)NH_2$, $N(CH_3)OH$, $N(CH_2CH_3)NH_2$, $NHOCH_3$, $NHN(CH_3)_2$, $N(CH_3)NHCH_3$, $NHNHCH_3$, $NHNHCOOCH_3$, $NHNHOCH_3$, $NHOCH_2CH_3$, and NHOH. However, especially preferred compounds include 2'-β-C-Methyl-$N^6$-amino-$N^6$-methyl-β-D-ribofuranosyladenosine, $N^6$-Ethyl-$N^6$-amino-9H-(2'-β-C-methyl-β-D-ribofuranosyl)purine, $N^6$-Hydroxy-$N^6$-methyl-9H-(2'-β-C-methyl-β-D-ribofuranosyl)purine, $N^6$-Hydroxy-9H-(2'-β-C-methyl-β-D-ribofuranosyl)purine, and $N^6$-Methoxy-9H-(2'-β-C-methyl-β-D-ribofuranosyl)purine.

Use of Contemplated Compounds

It is generally contemplated that contemplated synthetic procedures will provide 2-beta substituted-$N^6$-substituted nucleosides and nucleotides that may exhibit numerous biological activities. Especially contemplated biological activities include in vitro and in vivo inhibition of DNA and/or RNA polymerases, reverse transcriptases, and ligases. Therefore, contemplated nucleosides will exhibit particular usefulness as in vitro and/or in vivo antiviral agents, antineoplastic agents and immunomodulatory agents.

Particularly contemplated antiviral activities include at least partial reduction of viral titers of respiratory syncytial virus (RSV), hepatitis B virus (HBV), hepatitis C virus (HCV), herpes simplex type 1 and 2, herpes genitalis, herpes keratitis, herpes encephalitis, herpes zoster, human immunodeficiency virus (HIV), influenza A virus, Hants virus (hemorrhagic fever), human papilloma virus (HPV), yellow fever virus, and measles virus. The anti-HCV activity of the nucleosides and libraries can readily be tested by Replicon and BVDV cell-line based assays well known in the art (see e.g., V. Lohrarm, F. Korner, J.-O. Koch, U. Herian, L. Theilmann, R. Bartenschlager, "Replication of a Subgenomic Hepatitis C virus RNAs in a Hepatoma Cell Line", Sciences, 1999, 285, 110). Exemplary biological activity data and experimental conditions are described in our copending International patent application with the serial number PCT/US02/34026, which was filed Oct. 23, 2002, and which is incorporated by reference herein.

Especially contemplated immunomodulatory activity includes at least partial reduction of clinical symptoms and signs in arthritis, psoriasis, inflammatory bowel disease, juvenile diabetes, lupus, multiple sclerosis, gout and gouty arthritis, rheumatoid arthritis, rejection of transplantation, giant cell arteritis, allergy and asthma, but also modulation of some portion of a mammal's immune system, and especially modulation of cytokine profiles of Type 1 and Type 2. Where modulation of Type 1 and Type 2 cytokines occurs, it is contemplated that the modulation may include suppression of both Type 1 and Type 2, suppression of Type 1 and stimulation of Type 2, or suppression of Type 2 and stimulation of Type 1.

Where contemplated nucleosides are administered in a pharmacological composition, it is contemplated that suitable nucleosides can be formulated in admixture with a pharmaceutically acceptable carrier. For example, contemplated nucleosides can be administered orally as pharmacologically acceptable salts, or intravenously in a physiological saline solution (e.g., buffered to a pH of about 7.2 to 7.5). Conventional buffers such as phosphates, bicarbonates or citrates may be used for this purpose. Of course, one of ordinary skill in the art may modify the formulations within the teachings of the specification to provide numerous formulations for a particular route of administration. In particular, contemplated nucleosides may be modified to render them more soluble in water or other vehicle, which for example, may be easily accomplished with minor modifications (salt formulation, esterification, etc.) that are well within the ordinary skill in the art. It is also well within the ordinary skill of the art to modify the route of administration and dosage regimen of a particular compound in order to manage the pharmacokinetics of the present compounds for maximum beneficial effect in a patient.

In certain pharmaceutical dosage forms, prodrug forms of contemplated nucleosides may be formed for various purposes, including reduction of toxicity, increasing the organ or target cell specificity, etc. Among various prodrug forms, acylated (acetylated or other) derivatives, pyridine esters and various salt forms of the present compounds are preferred.

One of ordinary skill in the art will recognize how to readily modify the present compounds to pro-drug forms to facilitate delivery of active compounds to a target site within the host organism or patient. One of ordinary skill in the art will also take advantage of favorable pharmacokinetic parameters of the pro-drug forms, where applicable, in delivering the present compounds to a targeted site within the host organism or patient to maximize the intended effect of the compound.

In addition, contemplated compounds may be administered alone or in combination with other agents for the treatment of various diseases or conditions. Combination therapies according to the present invention comprise the administration of at least one compound of the present invention or a functional derivative thereof and at least one other pharmaceutically active ingredient. The active ingredient(s) and pharmaceutically active agents may be administered separately or together and when administered separately this may occur simultaneously or separately in any order. The amounts of the active ingredient(s) and pharmaceutically active agent(s) and the relative timings of administration will be selected in order to achieve the desired combined therapeutic effect.

EXPERIMENTS

Scheme 1

Synthesis of the Dess-Martin Reagent 1,1,1-Triacetoxy-1,1-Dihydro-1,2-Benziodoxol-3-(1H)-one (3)

A 3 L 3 neck RB flask was fitted with a mechanical stirrer, a heating mantle, a thermometer with adapter and a sodium hydroxide scrubber system. The vessel was charged with 100 g (0.403 mol) of 2-Iodobenzoic acid and 860 ml of 0.73 Molar sulfuric acid solution. The resultant white suspension was stirred and the pot temperature was increased to 55° C. at which point the vessel was charged with 87.3 g (0.523 mol) of potassium bromate added in small portions over a 40 min time period. After the addition was completed the pot temperature of the thick orangish-amber suspension was increased to 70° C., and the condition was maintained for a 3.5 h time period. The reaction mixture was allowed to cool to ambient conditions. The reaction mixture was cooled to −1° C. and maintained for 0.5 h. The filter cake was washed with 1 L of water, followed by 2×100 ml of ethyl alcohol, and then finally with 2×150 ml of diethyl ether. The cake was dried at high vacuum (~0.1 mmHg)/ambient temperature for 24 h. 101.56 g of white powder was obtained in 90% yield.

A 1 L 3 neck RB flask was fitted with a mechanical stirrer, a heating mantle, a thermometer with adapter, and a nitrogen inlet/outlet. The vessel was charged with 400 ml (4.24 mol) of acetic anhydride (4 ml/g) and 0.5 g (0.00263 mol) of p-toluenesulfonic acid-monohydrate under nitrogen atmosphere and stirring. The reaction mixture was charged with 100 g (0.357 mol) of 1-hydroxy-1,2-benziodoxol-3-(1H)-one. The resulting pale yellow suspension (pot temp=23° C.) was then heated to 80° C. for 2 h. The reaction mixture was allowed to cool to ambient temperature and then cooled to −2° C. The white suspension was stirred at −2° C. for 0.5 h and filtered. The filter cake was washed with 5×50 ml of diethyl ether and then quickly transferred to an amber bottle under an argon atmosphere. The bottle was subsequently stored under refrigeration at <5° C. 136.27 g of the desired product was obtained as a white solid in 90% yield.

Synthesis of 1',3',5'-Tri-O-benzoyl-D-ribofuranose (2) (Step 1)

Compound 2 was synthesized by a modified procedure based on the literature [Brodfuehrer, P. R.; Sapino, C., Jr.; Howell, H. G. J. Org. Chem. 1985, 50, 2598].

Synthesis of 1',3',5'-Tri-O-benzoyl-D-2-Ketoribofuranose 4 (Step 2)

A 3 L 3-necked RB flask was fitted with a mechanical stirrer, a thermometer with adapter, and a nitrogen inlet/outlet, to which was added 201 g (0.474 mol) of 1,1,1-triacetoxy-1,1-dihydro-1,2-benziodoxol-3-(1H)-one (Dess-Martin reagent, 3) and 1000 mL (15.60 mol) of dichloromethane under nitrogen atmosphere. The reaction mixture was cooled to −1° C., and 100 g (0.216 mol) of 1',3',5'-tri-O-benzoyl-D-ribofuranose (2) were added. The resulting reaction mixture was stirred at room temperature for 24 h and concentrated. The resultant residue was triturated with diethyl ether.

The resulting ether triturate was filtered through a pad of Celite, and then treated with 1 L of 1.0 M sodium thiosulfate solution. The organic phase was washed with sodium thiosulfate solution, and saturated sodium bicarbonate solution followed by brine. The organic phase was dried over magnesium sulfate and concentrated. The clear viscous pale yellow oily residue was subsequently dissolved in 2 L of dichloromethane. The solution was further treated with 500 g of magnesium sulfate for 24 h and concentrated. The residue was further dried under high vacuum to provide 95.47 g (96%) of the desired product 4 as a white foam. [Cook, G. P.; Greenberg, M. M. J. Org. Chem. 1994, 59, 4704-4706].

Synthesis of 1',2',3',5'-Tri-O-benzoyl-2-beta-C-methyl-D-ribofuranose (7) (steps 3 and 4)

A 5 L 3 neck RB flask was fitted with a mechanical stirrer, a thermometer with adapter, an additional funnel, a nitrogen inlet/outlet and a cooling bath. The vessel was charged with 2800 ml (26.74 mol) of diethyl ether (17 ml/g based on TiCl4) to which a continuous gentle stream of nitrogen was passed over. The reaction mixture was stirred and cooled to −78° C. 164.2 g (0.868 mol) of titanium (IV) chloride was added drop wise over 1 h. The resulting clear light yellow reaction mixture was treated with 289 ml (0.868 mol) of 3 Molar methyl magnesium bromide in diethyl ether drop wise. The reaction mixture was allowed to slowly warm to a pot temperature of −30° C. at which point 100 g (0.217 mol) of 1,3,5-tri-O-benzoyl-alpha-D-2-keto-ribofuranose in 200 ml of diethyl ether (2 ml/g) was added drop wise. The reaction mixture was allowed to stir at −30° C. for a 4 h. The organic phase was separated, and the aqueous phase was extracted with 3×2000 ml of diethyl ether. The combined organic phase was washed with water and then dried over magnesium sulfate. The organic solution was concentrated, and the residue was subsequently dried at high vacuum (~0.1 mmHg) and ambient temperature for a 24 h to provide 100.3 g (97%) of intermediate compounds 5 and 6 as a clear viscous oil, which was then used directly for the next step.

A 2 L 3 neck RB flask was fitted with a mechanical stirrer, a thermometer with adapter, an addition funnel, and a nitrogen inlet/outlet to which were added 6.63 g (0.0543 mol) of 4-dimethylaminopyridine and 500 ml (7.80 mol) of dichloromethane under nitrogen atmosphere. 85 ml (0.613 mol) of triethylamine were added followed by the addition of 12.6 ml (0.1086 mol) of benzoyl chloride drop wise. 25.87 g (0.0543 mol) of sugar intermediates 5 and 6 obtained above in 125 ml of dichloromethane (5 ml/g) were added dropwise. The resulting clear light amber reaction mixture was allowed to stir at ambient conditions for 3 h to complete the reaction (TLC analysis on silica gel, 4:1 Hex/EtOAc). The reaction mixture was diluted with 2.5 L of diethyl ether, and the clear pale amber solution was partitioned with a 750 ml portion of 1 Molar HCl solution in an extraction vessel. The organic phase was separated and washed with 2×500 ml of 1 Molar HCl solution, followed by a 500 ml of water and 2×500 ml portions of saturated sodium bicarbonate solution. The organic solution was dried over sodium sulfate and concentrated. The remaining residue was subsequently pumped at high vacuum/ambient temperature for a 14 h. The crude product was flashed through a 740 g plug of silica gel (20:1), packed and loaded with 9:1 hexane/ethyl acetate and eluted with a gradient from 9:1 to 4:1 hexane/ethyl acetate. The desired fractions were combined and evaporated on a rotary evaporator at 26 mmHg/bath temperature 35° C. and the remaining residue was pumped at high vacuum (~0.1 mmHg)/ambient temperature for a 14 h to provide 17.03 g (54%) of the desired product 7 as a pale yellow solid. 1H NMR (CDCl3) d 1.97 (s, 3H), 4.56 (dd, 1H, J=4.8, 12.0 Hz), 4.68 (dd, 1H, J=4.8, 12.0 Hz), 4.80 (m, 1H), 5.98 (d, 1H, J=8.0 Hz), 7.02-8.15 (m, 21H). [Wolfe, M. S.; Harry-O'kuru, R. E. Tetrahedron Lett. 1995, 36, 7611-7614; Harry-O'kuru, R. E.; Smith, J. M.; Wolfe, M. S. J. Org. Chem. 1997, 62, 1754-1759].

6-Chloro-9H-(2'-β-C-methyl-2',3',5'-tri-O-benzoyl-β-D-ribofuranosyl)purine (8) (Step 5)

Compound 8 was prepared based on the literature procedure with modification (P. Franchetti, L. Cappellacci, S. Marchetti, L. Trincavelli, C. Martini, M. R. Mazzoni, A. Lucacchini, M. Grifantrini, *J. Med. Chem.* 1998, 41, 1708-1715). To a stirred mixture of 6-chloropurine (1.82 g, 11.08 mmol) and 2'-β-C-methyl-1,2,3,5-tetra-O-benzoyl-D-ribose (6.44 g, 35.46 mmol) in anhydrous $CH_3CN$ (200 ml) under an Argon atmosphere was added 1,8-diazabicyclo[5.4.0]undec-7-ene (5.39 g, 35.46 mmol) at room temperature. The stirred mixture was cooled to 0° C. under Argon atmosphere. $Me_3SiOTf$ (10.49 g, 47.23 mmol) was added to the reaction mixture slowly during a 15 minute period at 0° C. The reaction mixture was then warmed to room temperature during a 30 minute period. The resulting reaction mixture was heated at 60° C. for 4 h and concentrated to dryness. The residue was partitioned between ethyl acetate and saturated $NaHCO_3$ (300/200 ml). The organic phase was separated, and the aqueous phase was extracted in ethyl acetate. The combined organic phase was washed with brine, dried over anhydrous sodium sulfate, and concentrated to dryness. The resultant residue was purified by flash chromatography on a silica gel column using hexane→EtOAc as the eluent. The pure fractions were collected and concentrated to dryness to provide 6.60 g (95%) of the titled compound 8. $^1$H NMR ($CDCl_3$) δ 1.61 (s, 3H), 4.77 (m, 1H), 4.93 (m, 2H), 6.21 (d, 1H), 6.82 (s, 1H), 7.30-7.62 (m, 9H), 7.94-8.12 (m, 6H), 8.30 (s, 1H), 8.79 (s, 1H).

6-Chloro-9H-(2'-β-C-methyl-β-D-ribofuranosyl) purine (9) (Step 6)

6-Chloro-9H-(2'-β-C-methyl-2',3',5'-tri-O-benzoyl-β-D-ribofuranosyl)purine (8) (6.5 g, 10.4 mmol) was dissolved in $CHCl_3$ (50 ml) and placed in a steel bomb. To this solution was added $MeOH/NH_3$ (200 ml). The bomb was closed and allowed to stir at room temperature for 8 h. The bomb was cooled to 0° C. and opened carefully. The reaction mixture was concentrated to dryness. The resultant residue was adsorbed on silica gel and placed on top of a silica gel column packed in $CHCl_3$. The column was eluted with a gradient of $CHCl_3$→MeOH. The required product was collected and concentrated to dryness to give 1.60 g (51%) of pure product 9 as a white solid. $^1$H NMR (DMSO-$d_6$) δ0.80 (s, 3H), 3.72 (m, 1H), 3.86 (m, 2H), 4.04 (m, 1H), 5.28 (m, 2H), 5.43 (s, 1H), 6.07 (s, 1H), 8.80 (s, 1H), 9.07 (s, 1H). $^1$H NMR ($CD_3OD$) δ0.89 (s, 3H), 3.87 (dd, 1H, J=12.6, 3.0 Hz), 4.04 (m, 2H), 4.22 (d, 1H, J=9.0 Hz), 6.09 (s, 1H), 8.19 (s, 1H), 8.55 (s, 1H); $^{13}$C NMR ($CD_3OD$) δ59.9, 72.9, 79.2, 83.3, 92.0.

2'-β-C-Methyl-$N^6$-amino-$N^6$-methyl-β-D-ribofuranosyladenosine (10) (Step 7)

A hot solution of 6-chloro-9H-(2'-β-C-methyl-β-D-ribofuranosyl)purine (9) (1.2 g, 4.0 mmol) in EtOH (100 ml) was diluted with $CHCl_3$ (40 ml). The resulting solution was cooled to room temperature. To this stirred solution was added N-methylhydrazine (1.06 ml, 20 mmol) under an Argon atmosphere. The reaction mixture was allowed to stir at room temperature for 12 h and concentrated to dryness. The resultant residue was adsorbed on silica gel, which was then placed on the top of a silica column packed in $CHCl_3$. The column was dated with a gradient of $CHCl_3$-MeOH (20:1 to 2:1). The desired fractions were collected and concentrated to dryness to give 0.6 g (49%, the optimized yield: 86%) of pure product 10 as a white solid. $^1$H NMR ($CD_3OD$) δ 8.45 (1H, s), 8.17 (1H, s), 6.08 (1H, s), 4.20 (1H, d, J=8.8 Hz); 4.08-4.02 (2H, at), 3.87 (1H, dd, J=2.75, 12.4 Hz), 3.62 (3H, s), 0.88 (3H, s). MS (EI) m/z 311 (M+1)$^+$.

Scheme 2

2'-β-C-Methyl-$N^6$-amino-$N^6$-methyl-β-D-ribofuranosyladenosine (10) (Step 8)

A mixture of 6-chloro-9H-(2'-β-C-methyl-2',3',5'-tri-O-benzoyl-β-D-ribofuranosyl)purine (8) (270 mg, 0.43 mmol) and N-methylhydrazine (10 mL) in EtOH (8 mL) was stirred at 90° C. (bath temperature) under argon atmosphere for 12 h. The reaction mixture was cooled and concentrated to dryness. The resultant residue was purified by flash chromatography on a silica gel column using a gradient of $CHCl_3$-MeOH (20:1 to 2:1) as eluent to give 122 mg (92%) of pure product 10 as a white foam. The product obtained this way shows the same spectroscopic properties as that obtained by the alternative procedure shown above.

$N^6$-Ethyl-$N^6$-amino-9H-(2'-β-C-methyl-β-D-ribofuranosyl)purine (11) (Step 9)

A mixture of 6-chloro-9H-(2'-β-C-methyl-2',3',5'-tri-O-benzoyl-β-D-ribofuranosyl)purine (8) (0.43 mmol) and N-ethylhydrazine (10 mL) in EtOH (8 mL) was stirred at 90° C. (bath temperature) under argon atmosphere for 12 h. The reaction mixture was cooled and concentrated to dryness. The resultant residue was purified by flash chromatography on a silica gel column using a gradient of $CHCl_3$-MeOH (20:1 to 2:1) as eluent to give pure product 11 as a white foam in 90% yield. ESMS m/z 325 (M+1)$^+$.

Alternatively, 6-($N^1$-Ethyl)hydrazino-(2'-β-C-methyl-β-D-ribofuranosyl) purine (11) can be prepared by the following procedure: Ethylhydrazine oxalate (4.15 g, 27.7 mmol) was suspended in EtOH (50 ml) and treated with N,N-diisopropylethylamine (9.56 ml, 55.00 mmol). This mixture was added into a stirred solution of 6-Chloro-(2',3',5'-tri-O-benzoyl-2'-β-C-Methyl-β-D-ribofuranosyl) purine (8) (2.5 g, 4.0 mmol) in CHCl₃ (15.0 ml) at room temperature. The stirring was continued at room temperature for 12 h and evaporated to dryness. The residue was partitioned between EtOAc (200 ml) and water (200 ml), and extracted in EtOAc. The organic extract was dried and concentrated to dryness. The residue was purified by flash chromatography over silica gel using a gradient of CHCl₃-MeOH (90:5) to give 2.5 g (98%) of pure product as a white foam.

The above product (2.5 g) was dissolved in CHCl₃ (10 ml) and diluted with EtOH (20 ml). N-Methyl hydrazine (20 ml) was added and heated at 95° C. under argon for 12 h. The reaction mixture was evaporated to dryness. The residue was purified by flash chromatography over silica gel using a gradient of CHCl₃-MeOH (90:5) to give 1.27 g (100%) of 11 as a white foam. ¹H NMR (CD₃OD) δ 8.48 (s, 1H), 8.22 (s, 1H), 6.09 (s, 1H), 4.00-4.24 (m, 5H), 3.86 (dd, 1H), 1.28 (t, 3H), 0.89 (s, 3H). MS (EI) m/z 325 (M+H)⁺.

N⁶-Hydroxy-N⁶-methyl-9H-(2'-β-C-methyl-β-D-ribofuranosyl)purine (12) (Step 10)

A mixture of 6-chloro-9H-(2'-β-C-methyl-2',3',5'-tri-O-benzoyl-β-D-ribofuranosyl)purine (8) (0.43 mmol) and N-methylhydroxyamine (2.5 mmol) in EtOH (20 mL) was stirred at 90° C. bath temperature under argon atmosphere for 12 h. The reaction mixture was cooled and concentrated to dryness. The resultant residue was purified by flash chromatography on a silica gel column using a gradient of CHCl₃-MeOH as eluent to give pure product 12 as a white foam in 80% yield. ¹H NMR (CD₃OD) δ 8.57 (s, 1H), 8.24 (s, 1H), 6.12 (s, 1H), 4.22 (d, 1H, J=8.8 Hz), 4.02-4.09 (m, 2H), 3.87 (dd, 1H, J=2.8, 12.2 Hz), 3.69 (s, 3H), 0.91 (s, 3H). MS (EI) m/z 312 (M+1)⁺.

N⁶-Hydroxy-9H-(2'-β-C-methyl-β-D-ribofuranosyl) purine (13) (Step 11)

Compound 8 (105 mg, 0.17 mmol) was dissolved in hydroxyamine in water (50% wt, 2 mL), and the reaction mixture was heated at 80° C. for 4 h. After the reaction was completed, the solvent was removed in vacuo. The residue was purified by flash chromatography on a silica gel column using CHCl₃:MeOH (20:1-2:1) as eluents to provide 30 mg of the desired product 13 in 58% yield. ¹H NMR (CD₃OD) δ8.58 (s, 1H), 8.05 (s, 1H), 6.09 (s, 1H), 4.19 (d, 1H, J=9.0 Hz), 4.08-3.99 (m, 2H), 3.85 (dd, 1H, J=2.59, 12.4 Hz), 0.93 (s, 3H). MS (EI) m/z 298 (M+1)⁺.

N⁶-Methoxy-9H-(2'-β-C-methyl-β-D-ribofuranosyl) purine (14) (Step 12)

A mixture of 6-chloro-9H-(2'-β-C-methyl-2',3',5'-tri-O-benzoyl-β-D-ribofuranosyl)purine (8) (0.43 mmol) and O-methylhydroxyamine (2.5 mmol) in EtOH (20 mL) was stirred at 90° C. (bath temperature) under argon atmosphere for 12 h. The reaction mixture was cooled and concentrated to dryness. The resultant residue was purified by flash chromatography on a silica gel column using a gradient of CHCl₃-MeOH as eluent to give pure product 14 as a white foam in 80% yield. ¹H NMR (CD₃OD) δ 8.20 (s, 1H), 7.61 (s, 1H), 5.98 (s, 1H), 4.17 (d, 1H, J=8.8 Hz), 3.97-4.06 (m, 2H), 3.80-3.88 (m, 1H), 3.84 (s, 3H), 0.95 (s, 3H). MS (EI) m/z 312 (M+1)⁺.

Thus, specific embodiments and applications of improved synthesis schemes for 2'-substituted nucleosides and their analogs have been disclosed. It should be apparent, however, to those skilled in the art that many more modifications besides those already described are possible without departing from the inventive concepts herein. The inventive subject matter, therefore, is not to be restricted except in the spirit of the appended contemplated claims. Moreover, in interpreting both the specification and the contemplated claims, all terms should be interpreted in the broadest possible manner consistent with the context. In particular, the terms "comprises" and "comprising" should be interpreted as referring to elements, components, or steps in a non-exclusive manner, indicating that the referenced elements, components, or steps may be present, or utilized, or combined with other elements, components, or steps that are not expressly referenced.

The invention claimed is:

1. A compound having a structure according to Formula I

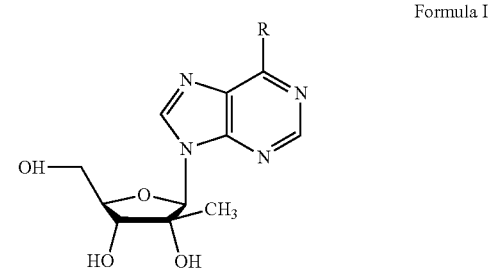

Formula I wherein R is selected from the group consisting of N(CH₂CH₃)NH₂, N(CH₃)OH, NHOCH₂CH₃, N(CH₃)NHCH₃, NHNHCH₃, and NHNHOCH₃.

2. The compound of claim 1, wherein R is NHNHOCH₃.

3. A compound having a structure according to Formula I

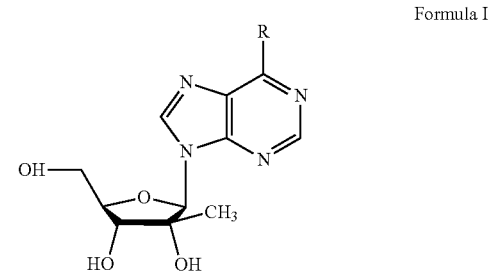

Formula I wherein R is selected from the group consisting of NHOCH₂CH₃, N(CH₃)NHCH₃, and NHNHCH₃.

4. The compound of claim 3, wherein R is NHOCH₂CH₃.
5. The compound of claim 3, wherein R is N(CH₃)NHCH₃.
6. The compound of claim 3, wherein R is NHNHCH₃.
7. A method of synthesizing a compound of Formula I,

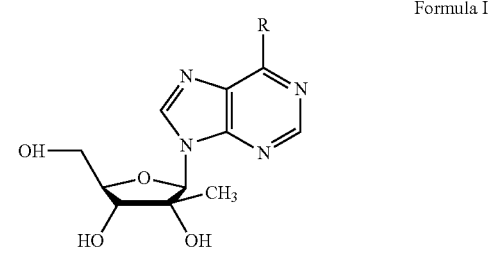

Formula I wherein R is selected from the group consisting of $N(CH_2CH_3)NH_2$, $N(CH_3)OH$, $NHOCH_2CH_3$, $N(CH_3)NHCH_3$, $NHNHCH_3$, and $NHNHOCH_3$, comprising reacting 6-Chloro-9H-(2'-β-C-methyl-β-D-ribofuranosyl)purine or 6-Chloro-9H-(2'-β-C-methyl-2', 3', 5'-tri-O-benzoyl-β-D-ribofuranosy)purine with a nucleophilic reagent selected from the group consisting of $NH(CH_2CH_3)NH_2$, $NH(CH3)OH$, $NH_2OCH_2CH_3$, $NH(CH_3)NHCH_3$, $NH_2NHCH_3$, and $NH_2NHOCH_3$.

8. The method of claim 7, wherein the reacting step comprises reacting 6-Chloro-9H-(2'-β-C-methyl-β-D-ribofuranosyl)purine with the nucleophilic reagent.

9. The method of claim 7, wherein the reacting step comprises reacting 6-Chloro-9H-(2'-β-C-methyl-2', 3', 5'-tri-O-benzoyl-β-D-ribofuranosyl)purine with the nucleophilic reagent.

10. The method of claim 7, wherein reacting 6-Chloro-9H-(2'-β-C-methyl- β-D-ribofuranosyl)purine or 6-Chloro-9H-(2'-β-C-methyl-2', 3', 5'-tri-O-benzoyl-β-D-ribofuranosyl) purine with the nucleophilic reagent occurs in a non-basic environment.

11. The method of claim 10, wherein the non-basic environment comprises at least one solvent selected from the group consisting of ethanol and methylene chloride.

12. The method of claim 7, wherein reacting 6-Chloro-9H-(2'-β-C-methyl-β-D-ribofuranosyl)purine or 6-Chloro-9H-(2'-β-C-methyl-2', 3',5'-tri-O-benzoyl-β-D-ribofuranosyl) purine with the nucleophilic reagent occurs under a protective atmosphere.

13. The method of claim 7, wherein reacting 6-Chloro-9H-(2'-β-C-methyl-β-D-ribofuranosyl)purine or 6-Chloro-9H-(2'-β-C-methyl-2', 3', 5'-tri-O-benzoylβ-D-ribofuranosyl)purine with the nucleophilic reagent occurs at a temperature of at least 40° C.

14. The method of claim 13, wherein the temperature is at least 70° C.

* * * * *